(12) United States Patent
Paris et al.

(10) Patent No.: US 6,331,205 B1
(45) Date of Patent: Dec. 18, 2001

(54) AQUEOUS VISCOUS COMPOSITIONS, WHETHER CLEAR OR NOT, FOR MAKING SOFT OR HARD CAPSULES, AND METHOD FOR MAKING FILMS FOR SUCH CAPSULES

(75) Inventors: Laurence Paris, 24, rue du Progres, F-03600 Commentry (FR); Fabrice Viaud, La Tessoualle (FR)

(73) Assignee: Laurence Paris, Commentry (FR)

( * ) Notice: Subject to any disclaimer, the term of this patent is extended or adjusted under 35 U.S.C. 154(b) by 0 days.

(21) Appl. No.: 09/403,647

(22) PCT Filed: Aug. 5, 1998

(86) PCT No.: PCT/FR98/01744

§ 371 Date: Dec. 6, 1999

§ 102(e) Date: Dec. 6, 1999

(87) PCT Pub. No.: WO99/07347

PCT Pub. Date: Feb. 18, 1999

(30) Foreign Application Priority Data

Aug. 8, 1997 (FR) .................................................. 97 10190

(51) Int. Cl.$^7$ ............................ C09D 105/00; C08J 5/00; A61K 9/48
(52) U.S. Cl. ..................................... 106/205.9; 106/205.2; 106/205.3; 106/205.31; 106/205.5; 106/205.7; 106/205.71; 106/205.72; 242/451; 242/452; 264/138; 264/280; 264/330
(58) Field of Search ............................ 106/205.2, 205.3, 106/205.31, 205.5, 205.71, 205.7, 205.72, 205.9; 424/451, 452; 264/138, 280, 330

(56) References Cited

U.S. PATENT DOCUMENTS 5,264,223  11/1993  Yamamoto et al. .
5,342,626   8/1994  Winston, Jr. et al. .

FOREIGN PATENT DOCUMENTS 0 592 130  9/1993  (EP) .
0 714 656  11/1995  (EP) .

OTHER PUBLICATIONS

Chemical Abstracts, vol. 126, No. 15, (Apr. 14, 1997), Abstract No. 203755, XP002063534.
Chemical Abstracts, vol. 110, No. 3, (Jan. 16, 1989), Abstract No. 22572, XP002063535.
Chemical Abstracts, vol. 103, No. 5, (Aug. 5, 1985), Abstract No. 36401, XP002063536.
Chemical Abstracts, vol. No. 109, No. 18, (Oct. 31, 1988), Abstract No. 156270, XP002063537.
Chemical Abstracts, vol. 104, No. 25, (Jun. 23, 1986), Abstract No. 223917, XP002063538.

*Primary Examiner*—David Brunsman
(74) *Attorney, Agent, or Firm*—Paul & Paul

(57) ABSTRACT

The invention concerns aqueous viscous compositions, whether clear or not, for making soft or hard capsules, and method for making films for such capsules (gelled capsules). Said compositions are in particular characterised in that they contain a single gelling agent consisting of a carrageenan, preferably an Iota carrageenan, whereof the concentration in the medium is higher than 5% of the medium which can be aqueous and oily. The invention also concerns a method for making films for such capsules which consists in dehydrating said films by oven drying or lyophilisation. The invention is applicable in pharmaceutics, cosmetics and dietetics.

25 Claims, No Drawings

AQUEOUS VISCOUS COMPOSITIONS, WHETHER CLEAR OR NOT, FOR MAKING SOFT OR HARD CAPSULES, AND METHOD FOR MAKING FILMS FOR SUCH CAPSULES

This is a 371 of PCT/FR98/01744 filed Aug. 5, 1998.

BACKGROUND OF THE INVENTION

Field of Invention

The present invention relates to the field of pharmaceutics, cosmetics and dietetics and has for objective to make pure carrageenan films for the manufacturing of hard and soft capsules or gelled capsules as well as a method for making the said film and soft capsules.

Discussion of the Background

Currently, the shell of both gelled capsules and capsules comprises gelatin as a base used either pure (for gelled capsules) or in combination with different substances, glycerine, sorbitol, etc, in the case of soft capsules.

However, due to major problems arising from the origin of gelatin, which comes mainly from bovine bones, the disease called "mad cow disease" or BSE (Bovin Spongiform Encephalitis) makes it crucial to find a substitute for such product.

Quite a number of products having gelifying characteristics or forming pseudo-colloidal solutions have been tested such as starch, cellulose, and hydrocolloids such as alginate, pectin, xanthane gum, etc.

The results obtained have not been conclusive in the case of hard and soft capsules, apart from the cellulosic by-products such as hydroxypropylmethyl cellulose for the manufacturing of gelled capsules.

Quite an amount of work has been carried out and has led to patents. Among these, the Japanese patents No. 09025228, No. 62289530, No. 61010508 and U.S. Pat. Nos. 5,342,626 mention carrageenans as a substitute for gelatin. But, in every case, they are always combined with another gelling agent such as mannans, galactomannans, agar, etc, and in fairly low concentrations in the order of 1 to 2%. The U.S. Pat. No. 5,342,626 and Japanese patent No 60012943 only mention Kappa carrageenans (K-carrageenans) even though it is known that films obtained from this type of carrageenans present an important power of retraction: synerese phenomenon working against the manufacturing of hard and soft capsules. Furthermore, this type of carrageenans does not enable to obtain a highly concentrated fluid solution in hot work as in cold work.

SUMMARY OF THE INVENTION

The aim of the present invention is to make the substitution of film for the hard and soft capsules with a shell based from a product of wholly vegetal origin which is much used in the food industry field, the carrageenans used pure as the one and single gelling agent of the composition of the shell with a concentration higher than 5% in solution in the medium. It is based on the fact that carrageenans heated between 50° C. and 100° C. have, when cooling, the characteristic to gelify and produce more or less breakable films depending on the type of carrageenans used. The Iota ($\iota$) type preferally adopted in the present invention does not present the synerese phenomenon and leads to films presenting a certain elasticity necessary to the manufacturing of soft capsules. The addition of a certain number of substances leads to the films obtained presenting similar physical characteristics to those of gelatin on the level of elasticity, thickness of films, time of disintegration, welding of films, as well as their appearance: transparent films, that can be coloured and cut to variable size.

The carrageenans have been known for over 600 years in the medical field and in foods in particular for their original characteristic which consisted in gelifying milk by a simple heating process. These are polysaccharides, polymers of galactose which are more or less sulfated.

The carrageenans that can be used in the present invention are, generally, extracts from different algae: *Chondrus crispus, Gigartina stellata, Gigartina acicularis, Gigartina skottsbergii, Gigartina pistillata, Gigartina chamissoi, Iridea, Eucheuma cottoni, Eucheuma spinosum.*

The extracting method implemented leads to different types of carrageenans of which the basic frame is a chain of D-galactoses alternately linked in $\alpha$—(1-3) and $\beta$—(1-4).

The different qualities are due to the quantity and to the position of the sulfates and the presence or not of a bridge 3, 6 anhydride on the galactose linked in 1 and 4.

DETAILED DESCRIPTION OF THE INVENTION

The different types of carrageenans that can be used in the present invention are Iota ($\iota$) carrageenans;

Lambda ($\lambda$) carrageenans;

Mu ($\mu$) carrageenans;

Nu ($\nu$) carrageenans;

the last two being in lower quantity in the wild.

The proportions of the different combinations vary according to the algae species.

The different carrageenans differ from one another by the proportion of sulfate groups present on the basic frame of the molecule.

The Lambda ($\lambda$) shapes present several sulfate groups in comparison with the Kappa ($\kappa$) shapes. The Iota ($\iota$) shapes are intermediary.

The Mu ($\mu$) and Nu ($\nu$) shapes are in lower quantity and are considered as impureties lowering the gelling effect of the Iota ($\iota$) and Kappa ($\kappa$) shapes.

The Lambda ($\lambda$) shape presents thickening characteristics but not gelling ones.

The Iota ($\iota$) carrageenans are, in the concept of the present invention, used on their own without the addition of another gelling agent, contrary to carrageenans used in the prior art of manufacturing films for hard or soft capsules. The concentration in carrageenans will preferably be higher than 5% of the medium with a maximum limit set to 80%. Advantageously, the volume of dissolution of the carrageenans can be water as well as a polyhydric alcohol blend of which the proportion in alcohol will vary between 0 and 60%.

The medium must be buffered so as to avoid a deterioration of the carrageenans in time under the effect of heat. In effect, in buffer medium and during a twenty-four hour period, a diminution of the viscosity of the medium through progressive hydrolysis of the carrageenans freeing acid radicals in the medium can be seen. This reaction is blocked when the medium is buffered. The pH value can vary between 5 and 12. Different buffering systems can be used citrates buffer: citric acid/citrates, phosphates buffer: sodium phosphate or potassium phosphate, phthalate buffer: potassium diphthalate/hydrochloric acid, borate buffer: boric acid/ sodium borate, carbonate buffer: bicarbonate/carbonate.

The agents favorising the dissolution of carrageenans belong to the alkaline class and the alkaline earth: sodium, calcium, potassium, etc, and are introduced in the medium in the shape of:

salts of hydrochloric, sulfuric, nitric, phosphoric, and citric acids and derived acids;

hydroxides.

The proportion of alkaline ions and alkaline earths that can be introduced in the medium varies between 0 and 50% in relation to the final volume of solution.

The elasticity of the films is obtained by the use of plasticizers which belong to the polyoxyls class: glycerol, sorbitol, maltodextrins, dextrose, mannitol, xylitol, polyoxyethylene glycol 400 to 6000, natural glycerides and hemi-synthetics and their derivatives, etc.

The quantity of these substances introduced in the solution of carrageenans is such that the coefficient of elasticity of the film can vary from 1 to 5 (1 to 5 times the initial length). The proportion of these substances that can be introduced in the medium varies between 0 and 30% in relation to the final volume of the solution.

The obtaining of a gradual disintegration time defined from the film is controlled by the introduction of tensio-actives in the medium, combined or not to substances presenting a power of disintegration. The tensio-actives used in the present invention can be non ionics. These are:

sorbitane esters: polysorbates, spans, tweens, etc.

fatty acids polyethoxyls: stearate of PEG 8 to stearate of PEG 100;

fatty polyethoxyled alcohols: blend of ethyl of monolaurate of PEG having from 4 to 23 oxyethylen groups on the polyoxyethylenic chain, etc.

glycol esters: stearate of methylglycol;

glycerol esters: monostearate of glycerol; etc.

esters of PEG;

saccharose esters;

ethyls of fatty alcohol and of PEG: Brij;

ethyls of alkyl phenol and of PEG;

tensio-actives presenting an amide function such as:
monoethanolamide of fatty acids of coprah, of lauric acid, etc.
diethanolamide of myristic acide, of lauric acid, etc.
mono-isopropanolamine of lauric acid.

ionics. Which are:

derived sulfates: the laurylsulfate of sodium and its derivatives;

derived sulfones dodecylsulfosuccinate of sodium and its derivatives;

quaternary ammoniums: cetyltrimethylammonium chloride, laurylpyridinium, distearyldimethylammonium, etc.

amphoterics: ammonium betaine of alkyldimethyl of coprah, derived from amids of fatty acid with betainic structure, lauryl-b-iminodipropionic acid and its derivatives, lauryl-myristyl-b-aminopropionic acid and its derivatives, etc.

The quantity of these substances introduced in the carrageenans solution is such that the disintegration time can vary from 3 minutes to 8 hours. These quantities can vary from 0% to 20% in relation to the final volume of solution. These tensio-actives can be combined with substances to improve the disintegration time, like wheat, rice, corn, manioc starch whether they have or not been subject to modifications. The quantities used can vary from 0 to 20% in relation to the final volume of solution.

Manufacturing additives such as preservatives, colourings and opaque agents can be introduced in the carrageenans solution. The proportion of preservatives can vary from 0 to 10% in relation to the final volume of solution. Colourings can dissolve in water or can be fixed on a alumine lacquer or any other support. The optimum level required is situated between 0.01 and 5% for colourings and from 0 to 10% for opaque agents in relation to the final volume of solution.

Solution made this way present a viscosity comprised between 200 and 1,000,0000 millipascals. From these solutions, films can be made which represent, at the time of pouring, a thickness of about 0.5 to 4.0 mm. After drying, the films represent a thickness ranging between 0.2 and 2.0 mm thick. Their retracting power after drying is situated between 0 and 50%.

Films obtained in this way can be lubricated to ease their implementation at the level of machines to make gelled capsules or to make soft capsules. The lubricants that can be used are:

classical edible oils (groundnut, sunflower, olive oils, etc.), emulsifiers such as esther of glycerol and polyoxyethylene glycol, triglycerids, esters of propylene glycol and their derivatives.

These lubricants can be used pure or diluted with a dilution of 10 to 75%.

Films obtained in this way for manufacturing whether it be gelled capsules or soft capsules can contain powders, solutions and suspensions of which the carriers are constituted by:

oils: groundnut oil, sunflower oil, olive oil, etc, and of the labrafil type;

polyoxyethyleneglycol: PEG 400, 600 etc.

propylene glycols emulsifiers polysorbates, soya lecithin;

suspension agents such as hydrogenated oils aqueous solutions containing a quaternairy ammonium.

The present invention also concerns the manufacturing process of films with an adaptation for obtaining soft capsules. Made by heating, the manufacturing of these films comprises three stages, that is:

preparation of the solution buffer by different constituents: dissolution agents, plasticizers, tensio-actives, preservatives and colourings;

the swelling of carrageenans in the basic solution;

and the dispersion if necessary of the opaque agent.

EXAMPLES

The following examples of embodiment are composition formulae given as non limitative examples.

Example No 1

| Example N° 1 | |
|---|---|
| Carrageenans | 15 g |
| Sodium chloride | 3 g |
| glycerine | 15 g |
| Water | 132 g |
| Example N° 2 | |
| Carrageenans | 15.0 g |
| Sodium hydroxide | 1.8 g |
| glycerine | 7.5 g |
| Water | 140.7 g |

-continued

| Example N° 3 | |
|---|---|
| Carrageenans | 15.00 g |
| Sodium hydroxide | 1.80 g |
| glycerine | 7.50 g |
| Orange-yellow S | 0.0 g |
| Water | 140.65 g |
| Example N° 4 | |
| Carrageenans | 15.00 g |
| Sodium hydroxide | 1.80 g |
| glycerine | 7.50 g |
| Polysorbate 80 | 1.50 g |
| Example N° 5 | |
| Carrageenans | 15.00 g |
| Potassium chloride | 2.00 g |
| glycerine | 7.50 g |
| Polysorbate 80 | 1.50 g |
| Sodium methyl parahydroxybenzoate | 0.12 g |
| Sodium propyl parahydroxybenzoate | 0.03 g |
| Water | 139.05 g |
| Example N° 6 | |
| Carrageenans | 39.500 g |
| Sodium chloride | 1.918 g |
| glycerine | 6.000 g |
| Polysorbate 80 | 6.000 g |
| Sodium methyl parahydroxybenzoate | 0.360 g |
| Sodium propyl parahydroxybenzoate | 0.090 g |
| Monosodium dihydrogen phophate | 0.390 g |
| Disodium hydrogen phosphate | 7.320 g |
| Water | 300.00 g |

In a 500 litres stainless steel container with double walls, fitted with an agitation and vacuum system:
- is introduced 300 kg of water, the sodium chloride, the monosodic phosphate, the disodic phosphate, the polysorbate 80, the glycerine and the preservatives,
- the vacuum is set up and the carrageenans are added with agitation with the temperature being maintained between 90° C. and 100° C. (the agitation speed is in the order of 1200 to 5000 revolutions per minute and preferably 2000 revolutions per minute),
- and this agitation is maintained until a more or less viscous mass is obtained. It can be kept for more than twenty four hours at 90° C.

The carrageenans solution obtained in this way is then transferred towards the machines for manufacturing gelled capsules or soft capsules where the storing temperature is maintained between 80° C. and 90° C.

In the case of soft capsules, the film obtained is then dehydrated by freezing at −4° C. during thirty minutes. Soft capsules are obtained in this way by sealing the films after lubrification according to an adaptation of the SCHERER method, by heating the dies at a temperature set between 70° C. and 100° C.

What is claimed is:

1. A viscous aqueous composition for making soft or hard capsules for aqueous and oily solutions, the composition comprising an aqueous medium and a single gelling agent consisting of an iota carrageenan, the concentration of the iota carrageenan being at least 5% of the aqueous medium, the composition further comprising at least one ion selected from the group consisting of the alkaline and alkaline earth ions.

2. A viscous aqueous composition according to claim 1, the concentration of the iota carrageenan being from 5% to 80% of the aqueous medium.

3. A viscous aqueous composition according to claim 1 wherein the aqueous medium comprises a polyhydric alcohol.

4. A viscous aqueous composition according to claim 1, wherein the composition is prepared by dissolving the iota carrageenan in an aqueous buffer medium.

5. A viscous aqueous composition according to claim 1, wherein the composition is prepared by dissolving the iota carrageenan in an aqueous medium having a pH of from 5 to 12.

6. A viscous aqueous composition according to claim 5 wherein the aqueous medium includes a buffer pair selected from the group consisting of citric acid/citrate, monosodium dihydrogen phosphate/disodium monohydrogen phosphate, monopotassium dihydrogen phosphate/dipostassium monohydrogen phosphate, bicarbonate/carbonate, potassium diphthalate/ hydrochloric acid, and boric acid/sodium borate.

7. A viscous aqueous composition according to claim 1 wherein the at least one ion selected from the group consisting of the alkaline and alkaline earth ions is selected from the group consisting of sodium, calcium and potassium ions.

8. A viscous aqueous composition according to claim 1 wherein the at least one ion selected from the group consisting of the alkaline and alkaline earth ions has a concentration from 0% to 50% of the aqueous medium.

9. A viscous aqueous composition according to claim 1 wherein the at least one ion selected from the group consisting of the alkaline and alkaline earth ions is provided by the corresponding compound selected from the group consisting of alkaline and alkaline earth hydroxides and alkaline and alkaline earth salts of hydrochloric acid, sulfuric acid, nitric acid, phosphoric acid, citric acid, and derivatives thereof.

10. A viscous aqueous composition according to claim 1 further comprising a plasticizing agent selected from the group consisting of sorbitol, glycerine, mannitol, xylitol, lactitol, polyoxyethylene glycols and their derivatives, and semi-synthetic glycerides and their derivatives.

11. A viscous aqueous composition according to claim 10 wherein the concentration of the plasticizing agent is from 0% to 30% of the final volume of the composition.

12. A viscous aqueous composition according to claim 1 further comprising a surfactant for controlling the dissolution of the soft or hard capsules, the surfactant being selected from the group consisting of non-ionic surfactants, ionic surfactants, and amphoteric surfactants.

13. A viscous aqueous composition according to claim 12 wherein the concentration of the surfactant is from 0% to 20% of the final volume of the composition.

14. A viscous aqueous composition according to claim 1 further including a disintegrating agent for controlling the dissolution of the hard or soft capsules, the disintegrating agent being selected from the group consisting of starches and derivatives thereof.

15. A viscous aqueous composition according to claim 14 wherein the concentration of the disintegrating agent is from 0% to 20% of the final volume of the composition.

16. A viscous aqueous composition according to claim 15 wherein the concentration of the colorants is from 0.01% to 5% of the final volume of the composition.

17. A viscous aqueous composition according to claim 1 further comprising a preservative and colorants.

18. A viscous aqueous composition according to claim 17 wherein the concentration of the preservative is up to 10% of the final volume of the composition.

19. A film formed from a viscous aqueous composition according to claim 1, the film further comprising a lubricant selected from the group consisting of oils, esters of glycerol, esters of polyoxyethylene glycol, triglycerides, esters of propylene glycol, and derivatives thereof.

20. A soft or hard capsule formed from a viscous aqueous composition according to claim 11.

21. A soft or hard capsule according to claim 20, the gel capsule being filled with an aqueous material or an oil.

22. A process for making soft or hard capsules from a viscous aqueous composition, the process comprising:
(a) preparing a hydrocolloidal solution by
(1) dispersing iota carrageenan at elevated temperature under vacuum in an aqueous medium to provide a hydrocolloidal solution, the concentration of the iota carrageenan being at least 5% of the aqueous medium, the medium containing alkaline ions or alkaline earth ions, a plasticzer, and a surfactant; and
(2) maintaining the solution between 50° C. and 90° C. during storage;
(b) forming a film for hard or soft capsules from the hydrocolloidal solution;
(c) forming and sealing capsules from the film, the sealing temperature of the capsules being maintained between 50° C. and 90° C. by means of preheated forming dies.

23. A process according to claim 22, the process further comprising treating the film by dehydrating it to bring the residual moisture level of the film to about 80% to 20% before forming and sealing the capsules.

24. A process according to claim 22 wherein the film is dehydrated by a heating step selected from oven drying and exposure to microwaves.

25. A process according to claim 22 wherein the film is dehydrated by freezing.

* * * * *